United States Patent [19]
Bloch et al.

[11] Patent Number: 4,645,626
[45] Date of Patent: Feb. 24, 1987

[54] PROCESS FOR THE PRODUCTION OF QUINIZARINE DERIVATIVES WHICH ARE DISUBSTITUTED IN THE 5- AND 8-POSITIONS BY HYDROXYL OR CHLORINE

[75] Inventors: Peter Bloch, Basel, Switzerland; Jean-Marie Adam, Saint-Louis, France

[73] Assignee: Ciba-Geigy AG, Basel, Switzerland

[21] Appl. No.: 765,621

[22] Filed: Aug. 14, 1985

Related U.S. Application Data

[63] Continuation of Ser. No. 639,972, Aug. 10, 1984, abandoned, which is a continuation of Ser. No. 255,070, Apr. 17, 1981, abandoned.

[30] Foreign Application Priority Data

Apr. 22, 1980 [CH] Switzerland ..................... 3106/80
Apr. 22, 1980 [CH] Switzerland ..................... 3107/80

[51] Int. Cl.$^4$ .................. C07C 50/24; C07C 50/34
[52] U.S. Cl. .................................. 260/383; 260/369; 260/384
[58] Field of Search .................. 260/383, 384, 369

[56] References Cited

U.S. PATENT DOCUMENTS 3,631,074 12/1971 Bien et al. ..................... 260/383
3,821,262 6/1974 Schoenauber et al. ............. 260/383

FOREIGN PATENT DOCUMENTS 2014566 10/1971 Fed. Rep. of Germany ...... 260/383
2758397 7/1978 Fed. Rep. of Germany ...... 260/383

Primary Examiner—Glennon H. Hollrah
Assistant Examiner—Raymond Covington
Attorney, Agent, or Firm—Wenderoth, Lind & Ponack

[57] ABSTRACT

The invention relates to a process for the production of 1,4,5,8-tetrahydroxyanthraquinone or 5,8-dichloro-1,4-dihydroxyanthraquinone by reacting phthalic anhydride with p-chlorophenol in oleum and in the presence of a boron catalyst, to give the quinizarine boron complex, and chlorinating this boron complex direct with a chlorinating agent, in the same reaction medium, to give the boron complex of dichloroquinizarine, and subsequently hydrolyzing this chlorinated boron complex to 1,4,5,8-tetrahydroxyanthraquinone or 5,8-dichloro-1,4-dihydroxyanthraquinone.

The novel process is environmentally and economically more advantageous than the sum of each of the individual process steps.

7 Claims, No Drawings

PROCESS FOR THE PRODUCTION OF QUINIZARINE DERIVATIVES WHICH ARE DISUBSTITUTED IN THE 5- AND 8-POSITIONS BY HYDROXYL OR CHLORINE

This is a continuation of application Ser. No. 639,972, filed 8/10/84 now abandoned which is a continuation of Ser. No. 255,070 filed 4/17/81 (now abandoned).

The present invention relates to a process for the production of 1,4,5,8-tetrahydroxyanthraquinone (hereinafter referred to as diquinizarine) by reacting phthalic anhydride with p-chlorophenol in oleum and in the presence of boron catalysts to give the boron complex of 1,4-dihydroxyanthraquinone, and then chlorinating this boron complex direct with chlorinating agents, in the same reaction medium, to give the boron complex of 5,8-dichloro-1,4-dihydroxyanthraquinone, and subsequently hydrolysing this chlorinated boron complex to diquinizarine.

The novel process proceeds in accordance with the following reaction scheme:

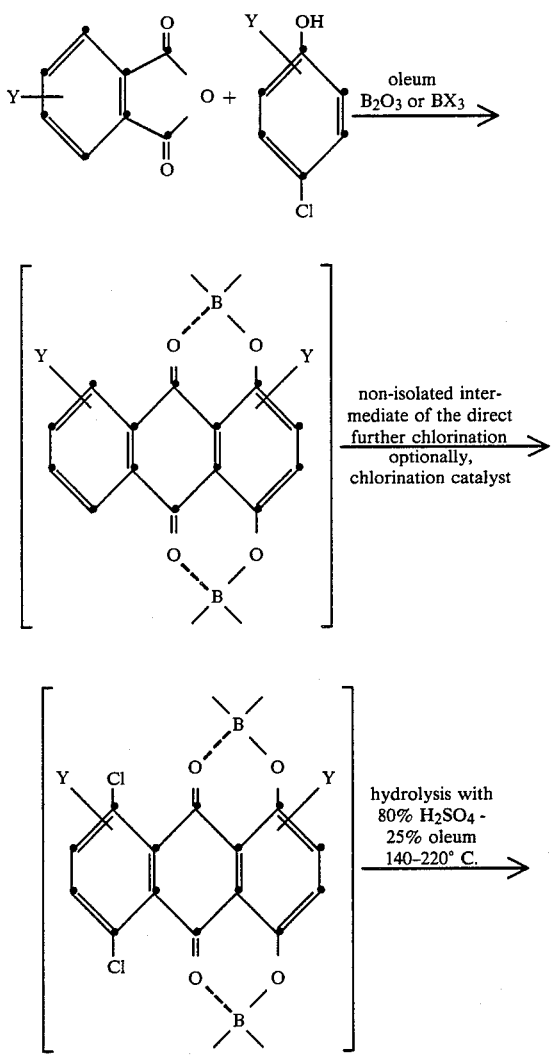

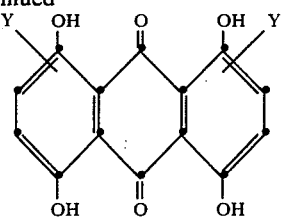

X = OH, halogen, O—acyl
Y = $C_1$–$C_4$ alkyl, halogen, preferably H,

The production of quinizarine from phthalic anhydride and p-chlorophenol is known from the prior art. It is also known from the prior art to obtain 5,8-dichloro-1,4-dihydroxyanthraquinone by chlorinating quinizarine, to hydrolyse 5,8-dichloro-1,4-dihydroxyanthraquinone to diquinizarine, and also to obtain 5,8-dichloroquinizarine by chlorinating quinizarine.

Up to now, however, these three processes were performed separately, as the acid concentration and temperature conditions of the reaction medium are of such importance for obtaining pure products and good yields in the individual steps that it was not be expected that combining the three reaction steps would solve the problem of carrying them out consecutively, under more favourable environmental and economic conditions, in the form of a unified process without isolation of the intermediates formed.

In the process for obtaining quinizarine by reacting phthalic anhydride with p-chlorophenol in sulfuric acid or oleum, in the presence of boric acid or, in accordance with German Offenlegungsschrift 2 014 566, or boric acid and a boron trihalide and/or of the complex compound of a boron trihalide, in the temperature range from 170° to 210° C., the quinizarine is isolated by diluting the reaction melt with water and separating the precipitated reaction product, if desired after treatment with alkali and in the presence of an oxidant.

The lower the temperature at which it is formed and the higher the concentration of sulfuric acid, the greater the purity of the 1,4-dihydroxyanthraquinone (quinizarine) obtained by the above method. However, at 180° C. the reaction proceeds so slowly that an economic production is jeopardised, whilst at 200° C. it proceeds at an acceptable rate but the purity of the product leaves something to be desired. If the reaction is carried out using a higher concentration of sulfuric acid, the purity of the reaction product increases but the yield decreases. The lower the concentration of the sulfuric acid, however, the greater the amount of acid which must be used. In each case, large amounts of waste sulfuric acid accumulate, the processing of which by neutralisation and the removal of the resultant substantial amounts of salt create both environmental and economic problems.

Further, the chlorination of quinizarine as intermediate is also carried out in concentrated sulfuric acid or oleum. During the subsequent working up, dilution of the reaction mixture again results in a large amount of waste sulfuric acid. The hydrolysis too requires a large amount of sulfuric acid.

The specific requirements in respect of reaction kinetics on the one hand, and the required high degree of purity of the quinizarine on the other, made it necessary to carry out each reaction under optimum reaction conditions, thus giving rise to the aforementioned drawbacks, especially the environmental ones. Accordingly, there was a genuine need for a unified process which avoids the above mentioned variations in the acid concentration and in which the three reaction steps can be carried out consecutively in the same reaction medium.

Surprisingly, it has now been found that 1,4-dihydroxyanthraquinone is obtained in a yield at least as good as and better than in the known processes, at higher reaction temperatures and using sulfuric acid of higher concentration in substantially lesser amounts, and that the subsequent chlorination can be carried out direct in the medium of the concentrated sulfuric acid or oleum, without isolation of the quinizarine obtained as intermediate, and with subsequent hydrolysis of the chlorinated product to give diquinizarine.

The novel process for the production of 5,8-dichloro- or 5,8-dihydroxyquinizarine by reacting phthalic anhydride with p-chlorophenol comprises carrying out the reaction in oleum and in the presence of $B_2O_3$, $H_3BO_3$ or boron halide, in the temperature range from 180° to 220° C., either continuously or discontinuously, and chlorinating the boron complex of 1,4-dihydroxyanthraquinone obtained as intermediate, direct without isolation, with a chlorinating agent, in the same reaction medium and and in the temperature range from 20° to 150° C., and either hydrolysing the chlorinated product by diluting the acid medium in the temperature range from 70° to 110° C. and isolating the 5,8-dichloroquinizarine thereby obtained, or by diluting the acid medium to a concentration of 80% $H_2SO_4$ to 25% oleum, in the temperature range from 140° to 220° C., and isolating the 5,8-dihydroxyquinizarine thereby obtained.

The novel process for the production of 1,4,5,8-tetrahydroxyanthraquinone further comprises carrying out the reaction of p-chlorophenol with phthalic anhydride in oleum and in the presence of $B_2O_3$, $H_3BO_3$ or boron halide, in the temperature range from 180° to 220° C., preferably from 200° to 210° C., either continuously or discontinuously, and chlorinating the boron complex of 1,4-dihydroxyanthraquinone obtained as intermediate, direct without isolation, with a conventional chlorinating agent and in the same reaction medium, if desired using a halogenating catalyst, in the temperature range from 20° to 150° C., and hydrolysing the chlorinated product by diluting the acid medium to a concentration of 80% $H_2SO_4$ to 25% oleum, in the temperature range from 140° to 220° C., to diquinizarine, if desired with the further addition of boric acid, and isolating it. The isolation of the reaction product is usually effected by lowering the concentration of oleum.

The novel process for the production of 5,8-dichloro-1,4-dihyroxyanthraquinone by reacting phthalic anhydride with p-chlorophenol furthermore comprises carrying out the reaction in oleum and in the presence of $B_2O_3$, $H_3BO_3$ or boron halide, in the temperature range from 180° to 220° C., either continuously or discontinuously, and chlorinating the boron complex of 1,4-dihydroxyanthraquinone obtained as intermediate, direct without isolation, with a conventional chlorinating agent, in the same reaction medium and in the temperature range from 20° to 150° C., and hydrolysing the chlorinated product by diluting the acid medium in the temperature range from 70° to 110° C., and isolating the hydrolysed product.

Both starting materials can be reacted in stoichiometric amounts. However, it is advantageous to use the cheaper phthalic anhydride in an excess of up to 1.5 times, especially 1.3 times, the stoichiometric amount.

The reaction is carried out as a rule at a weight ratio of oleum to phthalic acid of 1:1 to 4:1, advantageously 1.1 to 1.5:1, based on 35% oleum, and of boron trioxide to phthalic anhydride of 1:2 to 1:4. The concentration of the oleum is not of crucial importance and can, for example, be 70%.

Before the chlorination, it is advantageous to add further 50 to 70% oleum and/or chlorosulfonic acid to the reaction mixture.

Examples of suitable chlorinating agents are chlorine, chlorosulfonic acid, thionyl chloride or sulfuryl chloride. When using chlorine, a slight overpressure of up to 3 bar may be applied. It is advantageous to carry out the chlorination in the presence of a halogenating catalyst. Chlorosulfonic acid can also be used as solvent in the presence of oleum.

The novel process is carried out, for example, by adding boron trioxide, with stirring, to 35% oleum at 100° to 150° C., advantageously 120° to 130° C. Subsequently phthalic anhydride, and then p-chlorophenol, are added at 130° to 150° C., and the reaction mixture is heated, with thorough mixing, to 180° to 220° C., advantageously to 200° to 210° C., and kept at this temperature for 6 to 15 hours. When the reaction is complete, the reaction mixture is cooled to 160°-170° C. and during the subsequent cooling to about 50°-120° C., further 50 to 75% oleum and/or chlorosulfonic acid is added in an amount at least twice that of the oleum added at the start of the reaction, in order to keep the consistency of the reaction medium within the desired limits and at the same time to create the favourable conditions for the subsequent chlorination. A halogenation catalyst, e.g. $SCl_2$, but preferably iodine, is added, and then chlorination is effected in the temperature range from 20° to 150° C., preferably from 50° to 100° C., using one of the chlorinating agents specified above, until all the quinizarine is chlorinated. Excess chlorine is expelled and the reaction mixture is diluted with water, desirably to an $H_2SO_4$ concentration of 85 to 95%. The reaction mixture is then heated again for about 3 to 15 hours to 140°-220° C., and the diquinizarine is subsequently precipitated by further dilution with water, and isolated. It is advantageous to add a small amount of non-ionic surfactant to the reaction mixture. The addition of surfactant makes for a better crystal formation, thereby improving the filtering properties of the product and the flow properties of the dry goods.

If reaction substrates containing stable substituents are employed, then the products obtained are correspondingly substituted diquinizarines. Examples of such reaction substrates are $C_1$-$C_4$alkylated or halogenated phthalic anhydride and/or p-chlorophenol.

The novel process is much more efficient than the processes employed hitherto, using individual steps. Thus, for example, yields of over 90% (based on p-chlorophenol) of product of good quality are obtained, whereas the sum of the yields of the individual single step procedures is at most only 80%. Furthermore, the following operations commonly employed in the single step processes are no longer necessary:

pouring the reaction mixture of the boron complex of quinizarine onto ice or into water;
hydrolysing the boron complex of quinizarine to quinizarine;
preparing a solution of the boron complex of quinizarine for the second reaction step and heating the solution to the chlorination temperature;

preparing the boron complex of quinizarine in sulfuric acid;

filtering, washing and drying the quinizarine and dichloroquinizarine;

treating the wastewaters of the first two steps containing boric acid and sulfuric acid respectively.

The omission of the above operations results in considerable environmental and economic advantages, the most important of which are that the wastewater contains about 50% less boron compounds and, depending on the process variant employed, up to more than 70% less sulfuric acid, and that there is a saving in time, personnel, apparatus, and energy.

Dichloroquinizarine and diquinizarine obtained by the process of this invention can be reacted, without further purification, to dyes, e.g. by condensation with amines.

The following Examples illustrate the novel process, but imply no restriction to what is described therein. Parts are by weight, unless otherwise indicated.

EXAMPLE 1

A 500 ml sulfonating flask is charged with 77 parts of sulfuric acid monohydrate and 89 parts of 66% oleum are added, whereupon the temperature rises to 45° to 50° C. Then 38 parts of boron trioxide are added, with stirring, such that the temperature rises to 120°–125° C. The time required for this addition is about 20 minutes. A milky solution is obtained. The contents of the flask are heated to 150° and then, at 130° to 150° C., first 100 parts of phthalic anhydride and subsequently 64 parts of p-chlorophenol are added. The reaction mixture is then heated to 205°±2° C. and kept at this temperature for 14 hours.

The reaction mixture is then cooled to 160°–170° C. and, during the subsequent cooling to 100° C., 40 parts of 66% oleum are slowly added dropwise in order to ensure good stirrability. Another 325 parts of 66% oleum are then added dropwise—initially while cooling—at 70° C. After addition of 5 parts of finely pulverised iodine, elemental chlorine is introduced until chromatographic analysis of a sample shows that quinizarine is no longer present.

Excess chlorine is expelled from the reaction mixture by air or nitrogen. The concentration of sulfuric acid is then adjusted to 90% by dilution with water and the reaction mixture is stirred at 180° C. until no more diquinizarine can be detected by chromatographic analysis. The solution is poured into 200 parts of an approximately 6% aqueous sodium bisulfite solution and then 200 parts of a commercial polyether type surfactant are added. The batch is stirred for 1 to 3 hours at 85°–90° C. and then filtered. The filter cake is washed hot until neutral and dried, affording 125 parts of 1,4,5,8-tetrahydroxyanthraquinone (91.8% of theory, based on chlorophenol).

A reaction mixture prepared by the procedure of this Example is precipitated as described above, but without the addition of surfactant. The filtering properties of the product are markedly poorer.

EXAMPLE 1(a)

Variant method to obtain 5,8-dichloroquinizarine Chlorination is carried out as described in Example 1, then excess chlorine is expelled from the reaction mixture with nitrogen and the reaction mixture is poured into 2000 parts of an approximately 6% aqueous sodium bisulfite solution. Then 20 parts of a commercial polyether type surfactant are added and the mixture is stirred for 2 hours at 85°–90° C. and filtered. The filter cake is washed hot until neutral and dried, affording 145.3 parts of 5,8-dichloroquinizarine (94% of theory, based on chlorophenol). Chlorine content: 22.9% (theory: 22.94%).

COMPARISON EXAMPLE

A reaction mixture prepared by the procedure of Example 1 is poured into an aqueous bisulfite solution and stirred at 85°–90° C. for the same length of time as in Example 1, but without addition of surfactant. The product has markedly poorer filtering properties than in Example 1, is obtained in somewhat lower yield, and has a chlorine content of 24.5%.

EXAMPLE 2

38 parts of boron trioxide are added to 166 parts of 66% oleum and cautiously heated to 150° C. (exothermic reaction). Then 100 parts of phthalic anhydride and 64.3 parts of chlorophenol are added and the mixture is heated to 205° C. and stirred for 14 hours. The mixture is cooled to 160° C. and kept stirrable by the dropwise addition of 40 parts of 66% oleum during the subsequent cooling to 90° C. Then 400 parts of 66% oleum, 5 parts of iodine and finally 550 parts of chlorosulfonic acid are slowly added. The reaction mixture is then stirred at 90°–100° C. until a sample no longer shows the presence of quinizarine. The reaction mixture is then slowly poured into 3000 parts of ice-water, to which 150 parts of 40% bisulfite solution and 20 parts of surfactant have previously been added. The batch is refluxed for 3 hours, then filtered. The filter cake is washed and dried, affording 5,8-dichloroquinizarine in the same good yield as in Example 1(a).

EXAMPLE 3

To 435 parts of 9% oleum are added, in succession, 0.02 part of nitrobenzenesulfonic acid, 42.9 parts of $H_3BO_3$, 97.9 parts of phthalic anhydride and, when the solution has clarified, 64.3 parts of chlorophenol. The temperature of the mixture is raised over 5 hours to 195° C. and kept for 10 hours at this temperature, then cooled to 65° C. After addition of 5 parts of iodine and 800 parts of 66% oleum, chlorine is introduced at 65°–70° C. When the chlorination is complete, the batch is worked up as described in Example 1. Yield: 126 parts of 5,8-dichloroquinizarine.

EXAMPLE 4

To 200 parts of 20% oleum are added initially 38 parts of boron trioxide and then, at 120° C., 100 parts of phthalic anhydride and 64.3 parts of chlorophenol. The mixture is heated for 16 hours to 200° C., then cooled to 65° C. 400 parts of 66% oleum and 5 parts of iodine are added and then chlorine is introduced. When the chlorination is complete, the batch is worked up as described in Example 1. Yield: 128 parts of 5,8-dichloroquinizarine.

EXAMPLES 5 AND 6

The procedure of Example 2 is repeated, using the requisite amount of thionyl chloride and sulfuryl chloride respectively as chlorinating agent instead of chlorosulfonic acid. In each case an equally good final product is obtained in the same good yield as in Example 1(a).

EXAMPLE 7

The procedure of Example 1 is repeated, except that, after the chlorination, the sulfuric acid concentration is adjusted to 95% and the reaction mixture is stirred at 200° C. until no more starting material can be detected. 1,4,5,8-Tetrahydroxyanthraquinone is obtained in the same good yield as in Example 1.

EXAMPLE 8

By repeating the procedure of Example 7 and hydrolysing the 5,8-dichloroquinizarine with the addition of 25 parts of boric acid, 1,4,5,8-tetrahydroxyanthraquinone is obtained in good yield in half the reaction time.

What is claimed is:

1. A process for the production of 5,8-dichloro- or 5,8-dihydroxyquinizarine by reacting phthalic anhydride with p-chlorophenol, which process comprises reacting p-chlorophenol and phthalic anhydride in the stoichiometric ratio of 1:1 to 1:1.5 in oleum in the presence of $B_2O_3$, $H_3BO_3$ or boron halide, wherein oleum and phthalic anhydride are used in the weight ratio of 1:1 to 4:1 and boron compound, calculated as boron trioxide, and phthalic anhydride are used in the weight ratio of 1:2 to 1:4, carrying out the reaction in the temprature range from 180° to 220° C. either continuously or discontinuously, subsequently adding 50 to 70% oleum and/or chlorosulfonic acid to the reaction medium in an amount at least twice that of the oleum employed at the start of the reaction and chlorinating the boron complex of 1,4-dihydroxyanthraquinone obtained as intermediate, direct with isolation, without a chlorinating agent, in the same reaction medium and in the temperature range from 20° to 150° C., and either hydrolyzing the chlorinated product by diluting the acid medium in the temperature range from 70° to 110° C. and isolating the 5,8-dichloroquinizarine thereby obtained or by diluting the acid medium to a concentration of 80% $H_2SO_4$ to 25% oleum, in the temperature range from 140° to 220° C. and isolating the 5,8-dihydroxyquinizarine thereby obtained.

2. A process according to claim 1, which comprises hydrolysing the chlorinated product to diquinizarine by diluting the acid medium to a concentration of 80% $H_2SO_4$ to 25% oleum in the temperature range from 140° to 220° C., and isolating the hydrolysed product.

3. A process according to claim 1, which comprises hydrolysing the chlorinated product to 5,8-dichloroquinizarine by diluting the acid medium in the temperature range from 70° to 110° C., and isolating the hydrolysed product.

4. A process according to claim 1, wherein the condensation is carried out in the temperature range from 200° to 210° C. and the chlorination in the range from 50° to 100° C.

5. A process according to claim 1, wherein the chlorination is carried out in the presence of a halogenating catalyst.

6. A process according to claim 1, wherein chlorine is used as chlorinating agent.

7. A process according to claim 1, wherein a nonionic surfactant is added to the dilute acid medium.

* * * * *